US010358626B2

(12) United States Patent
Cattaneo et al.

(10) Patent No.: US 10,358,626 B2
(45) Date of Patent: Jul. 23, 2019

(54) PERFUSION FILTRATION SYSTEMS

(71) Applicant: Artemis Biosystems, Inc., Cambridge, MA (US)

(72) Inventors: Maurizio V. Cattaneo, Boston, MA (US); Remco A. Spanjaard, Brookline, MA (US)

(73) Assignee: Artemis Biosystems, Inc., Cambridge, MA (US)

( * ) Notice: Subject to any disclaimer, the term of this patent is extended or adjusted under 35 U.S.C. 154(b) by 79 days.

(21) Appl. No.: 15/485,866

(22) Filed: Apr. 12, 2017

(65) Prior Publication Data

US 2017/0292103 A1 Oct. 12, 2017

Related U.S. Application Data

(60) Provisional application No. 62/321,234, filed on Apr. 12, 2016.

(51) Int. Cl.
| | |
|---|---|
| C12M 1/00 | (2006.01) |
| C12M 1/12 | (2006.01) |
| C12N 5/00 | (2006.01) |
| B01D 61/14 | (2006.01) |
| B01D 61/18 | (2006.01) |
| B01D 61/20 | (2006.01) |
| B01D 63/02 | (2006.01) |
| B01D 63/06 | (2006.01) |
| B01D 71/26 | (2006.01) |

(52) U.S. Cl.
CPC .............. *C12M 29/10* (2013.01); *B01D 61/14* (2013.01); *B01D 61/18* (2013.01); *B01D 63/06* (2013.01); *B01D 71/26* (2013.01); *C12M 25/10* (2013.01); *C12M 29/04* (2013.01); *C12M 29/16* (2013.01); *B01D 61/20* (2013.01); *B01D 63/02* (2013.01); *B01D 2315/10* (2013.01); *C07K 2317/10* (2013.01); *C12N 5/00* (2013.01)

(58) Field of Classification Search
None
See application file for complete search history.

(56) References Cited

U.S. PATENT DOCUMENTS

| | | | | |
|---|---|---|---|---|
| 5,547,481 | A * | 8/1996 | Herding | B01D 39/1661 55/523 |
| 5,753,014 | A | 5/1998 | Van Rijn | |
| 8,119,368 | B2 | 2/2012 | Zijlstra et al. | |
| 2012/0315696 | A1* | 12/2012 | Luitjens | C12N 7/02 435/320.1 |
| 2013/0075321 | A1* | 3/2013 | Hobbs | B01D 71/34 210/321.8 |

(Continued)

FOREIGN PATENT DOCUMENTS

WO WO-2016/044670 A1 3/2016

OTHER PUBLICATIONS

International Search Report and Written Opinion for International Application No. PCT/US17/27176 dated Jul. 17, 2017.

(Continued)

*Primary Examiner* — Krishnan S Menon
(74) *Attorney, Agent, or Firm* — Foley Hoag LLP (57) ABSTRACT

Provided herein are tubular membrane filter elements, tangential flow filtration systems comprising such filter elements and methods of using such filter elements and filtration systems.

9 Claims, 4 Drawing Sheets

(56) References Cited

U.S. PATENT DOCUMENTS

2014/0087424 A1 3/2014 Crowley et al.
2014/0154745 A1 6/2014 Zijlstra et al.
2017/0002332 A1 1/2017 Boudeffa et al.

OTHER PUBLICATIONS

Ansorge et al., "Recent progress in lentiviral vector mass production," biochemical engineering journal, 48:362-377 (2010).
Ansorge et al., "Scalable lentiviral vector production using stable producer cell lines in perfusion mode," Engineering Conferences International (2018).
Higashikawa et al., "Kinetic analyses of stability of simple and complex retroviral vectors," Virology, 280:124-131 (2001).
Jouvenet et al., "Imaging the biogenesis of individual HIV-1 virions in live cells," Nature, 454(7201):236 (2008).
Mankarious et al., "The half-lives of IgG subclasses and specific antibodies in patients with primary immunodeficiency who are receiving intravenously administered immunoglobulin," The Journal of laboratory and clinical medicine, 112(5):634-640 (1988).
Merten et al., "Large-scale manufacture and characterization of a lentiviral vector produced for clinical ex vivo gene therapy application," Human gene therapy, 22(3):343-356 (2010).
Pelliccia et al., "Additives for vaccine storage to improve thermal stability of adenoviruses from hours to months," Nature communications, 7:13520 (2016).
Tiscornia et al., "Production and purification of lentiviral vectors," Nature protocols, 1(1):241 (2006).
Vázquez-Ramírez et al., "High-cell-density cultivations to increase MVA virus production," Vaccine, 36(22):3124-3133 (2018).
Yamada et al., "Lentivirus vector purification using anion exchange HPLC leads to improved gene transfer," Biotechniques, 34(5):1074-1080 (2003).

* cited by examiner

PERFUSION FILTRATION SYSTEMS

RELATED APPLICATIONS

This application claims the benefit of U.S. Provisional Application No. 62/321,234, filed on Apr. 12, 2016, the entire contents of which are hereby incorporated in their entirety.

BACKGROUND

Recent advances in molecular biology are positioning gene and gene-modified cell therapy on the cusp of an extraordinary revolution in patient care for presently unmet medical needs. However, the bioprocessing community is struggling to fulfill growing demands for bio-manufacturing capacity to make current good manufacturing practice (CGMP) viral vectors and particles, and virus-based vaccines.

Cell culture has generated considerable interest in recent years due to the revolution in genetic engineering and biotechnology. Cells are cultured to make proteins, receptors, vaccines, and antibodies for therapy, research, and for diagnostics. Traditionally, cell culture has been operated in a batch mode. In batch operation, the bioreactor is seeded with a small amount of cells and the cells are grown to a higher density. The cells secrete the product of interest and eventually die due to lack of nutrients at which point the culture is harvested. This method has several drawbacks. First, a large fraction of nutrients is wasted in simply growing up cells and are not used directly for making the product; secondly, product formation is often inhibited due to the buildup of toxic metabolic byproducts and lastly, critical nutrients are often depleted leading to low cell densities and consequently lower product yields. It has long been recognized that perfusion culture offers better economics. In this operation, cells are retained in the bioreactor, and the product is continuously removed along with toxic metabolic byproducts. Feed containing nutrients is continually added. This operation is capable of achieving high cell densities and more importantly, the cells can be maintained in a highly productive state for weeks. This achieves much higher yields and reduces the size of the bioreactor necessary or the footprint of the equipment compared to a batch operation, thus reducing costs. In addition, since the harvest is cell free, the initial cell separation step is eliminated, thus simplifying downstream purification steps. Perfusion operations have tremendous potential for growing the large number of cells needed for human cell and genetic therapy applications. The central problem in perfusion culture is how to retain the cells in the bioreactor while removing their desired, secreted product. People have used hollow fiber filtration as the method of choice due to the large surface area provided by the hollow fibers. However, filtration methods require some means to keep the filter from clogging over the required weeks of operation. Cross-flow filters containing hollow fiber membranes are thus typically used. Here a high tangential liquid velocity is used to keep the surface clean. Hollow fiber filters with pore sizes ranging from 10 nm to 1 μm have become the standard of practice for use in perfusion filters.

The traditional upstream manufacturing process for virus production using cell culture consists of a number of batch operations. Viral production entails three steps (1) the growth of "host" mammalian cells in a bioreactor followed by (2) viral production and (3) harvesting of the virus. Commonly these operations are done separately because of the need of different media for the cell growth and viral production phases. Lastly, the harvesting of the virus is commonly done by using depth filters as a separate harvesting step.

Perfusion using an alternating tangential flow system (see, e.g., U.S. Pat. No. 6,544,424, hereby incorporated by reference) offers a significant advantage to batch production of viruses. Alternating tangential flow (ATF) mode has enabled the growth of mammalian cells to a very high density without incurring the shear caused by standard tangential flow equipment which normally results in cell breakage and loss of yield. In U.S. Pat. No. 6,544,424 the ATF system includes two filter elements: a hollow fiber filter element, and a screen filter element. The hollow fiber filter has a membrane with a pore size of 0.2 micron, which allows the harvest of biological substances, such as monoclonal antibodies, with molecular sizes up to 10 nm. However, as is generally known to people working in the art, viral vectors and vaccines, such as retrovirus (e.g., lentivirus), adeno-associated virus (AAV), influenza virus, etc., do not appear in the harvest stream. This size exclusion by the hollow fiber membrane could be due to a combination of aggregation of the viral particles and/or surface interactions with the polyether sulfone hollow fiber membrane. It is known to people proficient in the art that commercially available hollow fiber filter elements having pore sizes of 0.2 μm do not function in an ATF perfusion system for harvesting viruses such as lentivirus (80-120 nm), adeno associated virus (AAV, 20-30 nm) or influenza virus (80-130 nm).

U.S. Pat. No. 6,544,424 also describes a filter element consisting of a screen with pore sizes between 20 μm and 70 μm for perfusion or media exchange of adherent cells using microcarriers. Here the microcarrier is retained by the screen filter element in the bioreactor, due to their relatively large size of 190 microns (GE Healthcare Life Sciences website). The sieve filter cannot be used for producing viruses by perfusion using suspension cells because the suspension cells would flow out of the perfusion filter and be depleted in the bioreactor. The benefit of using a suspension culture compared to a microcarrier based cell culture is that the suspension culture bioreactor and cross-flow filter assembly are more easily scalable. The screen filter element would defeat the purpose and allow passage of both viruses and suspension cells into the permeate and not act as a cell retention device which is its intended purpose.

Unfortunately, a perfusion process which allows both media exchange as well as viral recovery has eluded investigators. Therefore, there is a need for a filter element that would retain cells in suspension as well as allow passage of viral particles into the harvest stream as part of an alternating tangential flow system.

SUMMARY

Provided herein are tubular membrane filter elements, tangential flow filtration systems comprising such filter elements and methods of using such filter elements and filtration systems.

In certain aspects provided herein is a tubular membrane filter element comprising a plurality of tubular porous membranes (e.g., 2, 3, 4, 5, 6, 7, 8, 9, 10, 11, 12, 13, 14, 15, 16, 17, 18, 19, 20 or more tubular porous membranes). In some embodiments, each of the plurality of tubular porous membranes are made of porous plastic (e.g., polyethylene, high density polyethylene, Ultra-high-molecular-weight polyethylene (UHMWPE), polypropylene (PP), polytetrafluoroethylene (PTFE), polyvinylidenefluoride (PVDF), ethylvinylacetate (EVA), polycarbonate, nylon 6, thermoplastic urethane (TPU), polyethersulfone (PES), polysulfone (PS), preferably high-molecular-weight polyethylene (UHM-WPE), or combinations thereof).

In some embodiments of the tubular membrane filter elements provided herein, at least 80%, at least 85%, at least 90%, at least 95%, at least 96%, at least 97%, at least 98%, at least 99%, at least 99.5%, at least 99.9%, at least 99.99% or 100% of the pores in each of the plurality of tubular porous membranes have a size of about 1 µm to about 20 µm, 5 µm to about 15 µm or 7 µm to about 12 µm. In some embodiments, at least 80%, at least 85%, at least 90%, at least 95%, at least 96%, at least 97%, at least 98%, at least 99%, at least 99.5%, at least 99.9%, at least 99.99% or 100% of the pores have a size of at least 1 µm, at least 2 µm, at least 3 µm, at least 4 µm, at least 5 µm, at least 6 µm or at least 7 µm. In some embodiment, at least 80%, at least 85%, at least 90%, at least 95%, at least 96%, at least 97%, at least 98%, at least 99%, at least 99.5%, at least 99.9%, at least 99.99% or 100% of the pores have a size of no more than 20 µm, no more than 20 µm, no more than 19 µm, no more than 18 µm, no more than 17 µm, no more than 16 µm, no more than 15 µm, no more than 14 µm, no more than 13 µm or no more than 12 µm. In some embodiments, the pore size is such that viruses (e.g., lentiviruses, adeno-associated viruses (AAV), and/or influenza viruses) pass through the membrane but mammalian cells are retained.

In some embodiments of the tubular membrane filter elements provided herein, each of the plurality of tubular porous membranes has an internal diameter of about 1 mm to about 10 mm, about 1 mm to about 5 mm, or about 3 mm to about 4 mm. In some embodiments, each of the tubular porous membranes has an internal diameter of about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm or about 20 mm.

In certain embodiments of the tubular membrane filter elements provided herein, the plurality of tubular porous membranes are enclosed within a casing (e.g., a nonporous plastic casing, a metal casing). In some embodiments the casing has an internal diameter of about 10 mm to about 50 mm, about 20 mm to about 30 mm or about 25 mm. In some embodiments, the casing has an internal diameter of about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 mm. The casing can have a diameter up to 10 cm for a pilot scale unit and up to 30 cm for a commercial unit.

In certain aspects, provided herein is a tangential flow filtration system (e.g., an alternating tangential flow system) comprising at least one filter element provided herein (e.g., at least 1, 2, 3, 4, 5, 6, 7, 8, 9, 10, 50, 100 or 200 filter elements). In some embodiments, a permeate flows through the pores of the tubular porous membranes in the filter elements into the casing in which the filter elements are enclosed. In some embodiments, the permeate comprises a virus e.g., a lentivirus, an adeno-associated virus (AAV), and/or an influenza virus. In some embodiments, mammalian cells are retained within the tubular porous membranes. In certain embodiments, the tangential flow filtration system further comprises a cell culture system connected to the at least one filter element such that a cell culture flows through the interior of the plurality of tubular porous membranes of at least one filter element. In some embodiments, the cell culture system comprises a bioreactor. In certain embodiments, the filtration system further comprising a pump (e.g., a diaphragm pump).

In certain embodiments, provided herein are methods of filtering a cell culture media comprising passing a cell culture media comprising mammalian cells and a virus e.g., a lentivirus, an adeno-associated virus (AAV), and/or an influenza virus through the single or plurality of tubular porous membranes of a filter element provided herein, such as a filter element in a tangential flow filtration system provided herein, such that the mammalian cells are retained within the tubular porous membrane and at least a portion of the virus passes through the pores of the tubular porous membrane. In some embodiments, the method is a tangential flow perfusion method, such as an alternating tangential flow perfusion method.

BRIEF DESCRIPTION OF THE FIGURES

FIG. 2 is a schematic diagram of the side view (left) and the front view (right) of an exemplary tubular membrane filter element according to certain embodiments provided herein. The members 100 refers to the ends of an exemplary filtration system through which the tubular membrane filter element may be connected to a closed system containing a fluid, preferably a cell culture media, preferably synthetic, which comprises at least a permeate to remove from the fluid. For example, the tubular membrane filter element may be connected to a cell incubation system (e.g., culturing flasks, fermentation tanks, etc.) so that the cell culture may flow through, optionally driven by a certain force (e.g., under the pressure of a diaphragm pump), the tubular membrane filter element inside the casing of the filtration system. The members 200 refer to at least one outlet (two in the shown exemplary system) connecting to the inside area of the casing of the filtration system, which may be filled with a fluid, preferably cell culture media, preferably synthetic. After filtration, the at least one permeate may be released through the pores on the tubular membrane filter element into the inside area of the casing of the filtration system, and then be collected through the members 200.

DETAILED DESCRIPTION

Provided herein are tubular membrane filter elements, tangential flow filtration systems comprising such filter elements and methods of using such filter elements and filtration systems. As disclosed herein, a tubular membrane cross-flow filter made with multiple porous plastic membrane tubes allows for the efficient harvesting of viruses from a virus-producing suspension culture In some embodiments, the filtration systems provided herein can include any size of the porous plastic tubular membranes including internal diameter, outside diameter, length, number of tubes, length and diameter of casing for the efficient harvesting by cross flow, tangential flow or alternating tangential flow filtration as part of a perfusion system for culturing mammalian cells and harvesting viral products. In some embodiments, the number of tubes present in the filter element will directly impact the permeate flux, hence the viral production rate. Scaling up the filter element can be done by simply increasing the number of tubes for the same length of tubing and keeping the internal diameter of the tubing constant. Alternatively, the number, grouping, length, internal and/or outside diameter of the tubular membranes can be adjusted to meet the required processing times. In certain embodiments, the use of the filter elements disclosed herein allow for the harvesting of viruses from the cell culture to be performed in a closed system. Having a closed operation has the benefit of reducing the exposure to pathogenic viruses for manufacturing personnel, and reducing risk of contamination and failed runs.

In certain embodiments, the perfusion filters disclosed herein can be used to implement cell growth, media exchange as well as harvest viruses from the cell culture. Hence, in some embodiments the filter elements provided herein reduces the three operations of cell growth, virus production and virus harvesting into a single closed operation.

In some embodiments, the macroporous filter element of the present invention is able to retain mammalian cells present in the cell culture in a perfusion mode while providing total harvesting of viral particles in a closed system, using one single filter element for both the cell culturing, infection and harvesting phases of viral production, thus minimizing the risk of contamination and reducing the risk of exposure for operators of the cell culture facility.

A perfusion process is described in U.S. Pat. No. 6,544,424, which is hereby incorporated by reference. Although this document mentions that this process may be used for perfusion culturing of animal cells, it does neither disclose nor suggest the metabolic control used to maintain a low flow perfusion flow concentration found in the present invention.

A continuous process integrating perfusion and downstream capture chromatography offers better economics compared to batch processes of culturing cells. In this operation, cells are retained in the bioreactor, and the product is continuously removed along with toxic metabolic byproducts. Feed, containing nutrients is continually added. This operation is capable of achieving high cell densities and more importantly, the cells can be maintained in a highly productive state for weeks. This achieves much higher yields and reduces the size of the bioreactor necessary. It is also a useful technique for cultivating primary or other slow growing cells. Perfusion operations have tremendous potential for growing the large number of cells needed for human cell and genetic therapy applications.

As used herein, perfusion culturing of cells has its conventional meaning in the art, i.e. it means that during culturing cells are retained by a filter module in which there is an outflow of liquid void of cells "the perfusate". A person skilled in the art knows how to determine the outflow or perfusion rate. Perfusion culturing results in the production of a continuous flow. Filter modules comprising tubular membranes are commercially available from for example Spectrum Laboratories (SpectrumLabs).

As used herein, "alternating tangential flow within the filter module" means that there is one flow in the same direction as (i.e. tangential to) the membrane surfaces of the hollow fibers, which flow is going back and forth, and that there is another flow in a direction substantially perpendicular to said filter surface. Tangential flow can be achieved according to methods known to the person skilled in the art. For example, in U.S. Pat. No. 6,544,424 it is described that alternating tangential flow can be achieved using one pump to circulate the cell culture over a filter module comprising hollow fibers and another pump to remove the liquid having a lower cell density than prior to the filter separation. In the process of the present invention, the separation device is a filter module comprising a tubular membrane which is manufactured through a different process and which has distinctly different properties and functionality.

In some embodiments, the mesh size in the membrane is chosen such that the size of the pores in the mesh is close to the diameter of the cells, ensuring a high retention of cells while cell debris can pass the filter. In some embodiments, the mesh size is between 1 $\mu M$ and 20 $\mu M$. Cells which can be used to produce the viral vector or viral vaccine are in principle all cells known to the person skilled in the art, which have the ability to produce a biological product. In some embodiments, the cells are animal cells, in particular mammalian cells. Examples of mammalian cells include CHO (Chinese Hamster Ovary) cells, hybridomas, MDCK (Madin Derby Canine Kidney) cells, myeloma cells, human cells, for example HEK-293 cells, HeLa cells, human lymphoblastoid cells, E1 immortalized HER cells and PER.C6 cells. Mammalian cells such as HEK293 have diameters ranging from 11 $\mu m$ to 15 $\mu m$ diameter, HeLa (12 $\mu m$-14 $\mu m$), CHO (14 $\mu m$-17 $\mu m$) and MDCK (13 $\mu m$-15 $\mu m$) (www.BioNumbers.org) are mostly retained by the tubular membrane of this inventions.

In some embodiments, a viral vector is produced by a host cell. The viral vector can suitably be produced in the perfusion culturing of the cell and can in principle be done for all viral substances, live viruses and genetically-engineered viral vectors (viral particles) used in gene therapy, etc. According to the certain embodiments, a viable cell density is a density of at least $10 \times 10^6$ cells per mL, $20 \times 10^6$ cells per mL, $40 \times 10^6$ cells per mL, at least $50 \times 10^6$ cells per mL or at least $60 \times 10^6$ cells per mL. In certain embodiments, a suitable upper limit in the cell density may lie around $70 \times 10^6$ cells per mL.

In some embodiments, the high cell density of the cell culture is accompanied by a high cell viability. A high cell viability is a viability of at least 90%, at least 95%, at least 97%, or at least 99%. It is to be understood that high viable cell density and high cell viability are reached after a certain period of perfusion culturing, generally when the cells have reached a steady state, for mammalian cells typically 12 to 25 days after the initiation of perfusion culturing.

In certain embodiments, the pH, temperature, dissolved oxygen concentration and osmolarity of the cell culture medium are in principle not critical and depend on the type of cell chosen. In some embodiments, the pH, temperature, dissolved oxygen concentration and osmolarity are chosen such that it is optimal for the growth and productivity of the cells. In certain embodiments, the optimal pH is between 6.8 and 7.2, the optimal temperature between 32 and 39° C., the optimal osmolarity between 260 and 400 mOsm/kg. Generally, a cell culture medium for mammalian cells comprises amino acids, vitamins, lipids, salts, detergents, buffers, growth factors, hormones, cytokines, trace elements and carbohydrates. Examples of amino acids are all 20 known proteinogenic amino acids, for example histidine, glutamine, threonine, serine, methionine. Examples of vitamins include: ascorbate, biotin, choline-Cl, myo-inositol, D-panthothenate, riboflavin. Examples of lipids include fatty acids, for example linoleic acid and oleic acid; soy peptone and ethanol amine. Examples of salts include magnesium salts, for example $MgCl_2.6H_2O$ $MgSO_4$ and $MgSO_4.7H_2O$ iron salts, for example $FeSO_4.7H_2O$, potassium salts, for example $KH_2PO_4$, KCl, sodium salts, for example $NaH_2PO_4$, $Na_2HPO_4$ and calcium salts, for example $CaCl_2.2H_2O$. Examples of detergents include Tween 80 and Pluronic F68. An example of a buffer is HEPES. Examples of growth factors/hormones/cytokines include IGF, hydrocortisone and (recombinant) insulin. Examples of trace elements are known to the person skilled in the art and include Zn, Mg and Se. Examples of carbohydrates include glucose, fructose, galactose and pyruvate.

In some embodiments, the viral vector or vaccine in the outflow of the perfusion filter may be further purified in so-called downstream processing. Downstream processing usually comprises several purification steps in varying combinations and order. Examples of purification steps in the downstream processing are separation steps (e.g. by affinity chromatography or hydrophobic interaction chromatography), steps for the concentration of the viral vector (e.g. by ultrafiltration or diafiltration), steps to exchange buffers and/or steps to remove viruses (e.g. by virus filtration and/or pH shift).

The term "cross-flow" as used herein is meant to include a tubular membrane filter incorporated into a tangential flow system such as an alternating tangential flow system.

The term "hollow fiber" as used herein is meant to include polymer tubes made by an extrusion process called spinning. Extrusion process tend to form fairly tight pore membranes with pore sizes less than 1 µm. Hollow fiber membrane are small porous fibers which are bundled together and sealed in a chamber to produce a hollow fiber membrane filter. The feed is pumped through the fibers and the permeate flows through the tubing in the chamber.

The term "tubular membrane" as used herein is meant to include porous plastic membranes made by sintering with pore sizes greater than 1 µm and where the internal diameter of the tube is at least 1 mm, most preferably at least 3 mm and preferably the internal diameter of the tube is at most 10 mm, most preferably at most 4 mm.

The term "microporous" is meant herein to include all membranes with pore sizes less than 1 µm.

The term "macroporous" is meant herein to include all membranes with pore sizes between 1 µm and 20 µm.

The macroporous tubular membrane as used herein is made by a sintering process which allows the formation of fairly wide pores with sizes ranging from 1 µm to 20 µm. The "macroporous membrane" as used herein is meant to include membranes with pore sizes that are chosen such that the virus particle is able to perfuse through the membrane and the cells is retained by the membrane and returned to the bioreactor.

The term "screen" is meant herein to include all membranes with pore sizes greater than 20 µm. A screen filter as used herein is meant to address the culturing of adherent cells using large size microcarriers such as Cytodex® (GE Healthcare). Screens with pores or openings of 70 µm are generally used in conjunction with an ATF system with the purpose of retaining the microcarriers such as cytodex (size of 170 µm) inside the bioreactor.

The term "perfusion" as used herein is meant as a process for growing mammalian cells to a high cell density by continuously adding fresh media to the cell culture and removing toxic metabolites and product such as viral particles in the permeate side of a tangential flow filter element. Perfusion is also a very convenient system method for media exchange between the cell growth phase and the production phase and is ideal for use in a commercial setting because it greatly diminishes the risk of contamination and consequently, failed runs.

The term "alternating tangential flow" as used herein is meant that there is one flow in the same direction as (i.e., tangential to) the filter surface(s), which flow is going back and forth, and that there is another flow in a direction substantially perpendicular to said filter surface which is called the permeate. Alternating tangential flow can be achieved according to methods known to the person skilled in the art (for example as described in U.S. Pat. No. 6,544,424).

In some embodiments, the pore size of the filter is chosen such that the size of the pores of the filter is larger than at least a factor 2 or at least a factor 3 larger than the diameter or size of the product, ensuring a high concentration of product in the permeate flow. As shown in Table 1 and Table 2, which correspond to exemplary tubular membranes described herein, the pore size of the porous plastic membrane tubule can be at least 1 µm, at least 5 µm or at least 7 µm and/or the pore size of the filter/membrane is at most 20 µm, at most 15 µm or at most 12 µm.

TABLE 1

Material, pore size and dimension of tubular membranes utilized for fabrication of cross-flow filter indicating the outer diameter (OD), inner diameter (ID) and wall thickness (WT) of the tubular membranes.

| Material | Pore Size | Dimensions | Length |
|---|---|---|---|
| Polyethylene | 5-15 µm | ¾", OD & ⅛" WT | 10" |
| Polyethylene | 5-15 µm | 0.5", OD & 0.105 WT | 10" |
| Polyethylene | 5-15 µm | OD 0.25", ID 0.125" | 16" |
| Polyethylene | 5-15 µm | OD 0.25, ID 0.125" | 24" |

TABLE 2

Various configurations of tubular membrane filters

| Inner Tube, id (cm) | length (cm) | Effective length = tube length − potting, (cm) | internal surface area, (sq. cm) | Outer Casing id (cm) |
|---|---|---|---|---|
| 1.27 | 25.4 | 23.495 | 93.69 | 2.54 |
| 0.635 | 25.4 | 23.495 | 93.69 | 2.54 |
| 0.3175 | 40 | 38.735 | 115.85 | 3.175 |
| 0.3175 | 40 | 38.735 | 347.55 | 3.175 |
| 0.3175 | 60 | 58.735 | 409.89 | 3.175 |
| 0.3175 | 63.5 | 60 | 527.00 | 2.54 |
| 0.3175 | 63.5 | 60 | 5000 | 10 |
| 0.3175 | 63.5 | 60 | 25,000 | 30 |

Figure 1:
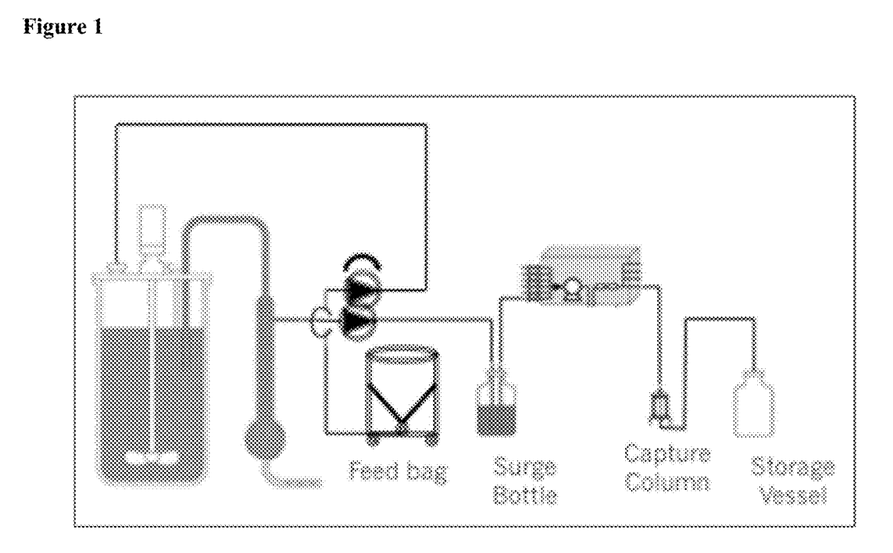
FIG. 1 shows a schematic diagram of an exemplary continuous manufacturing system for production of viral vectors and viral vaccines according to certain embodiments provided herein.
Figure 2:
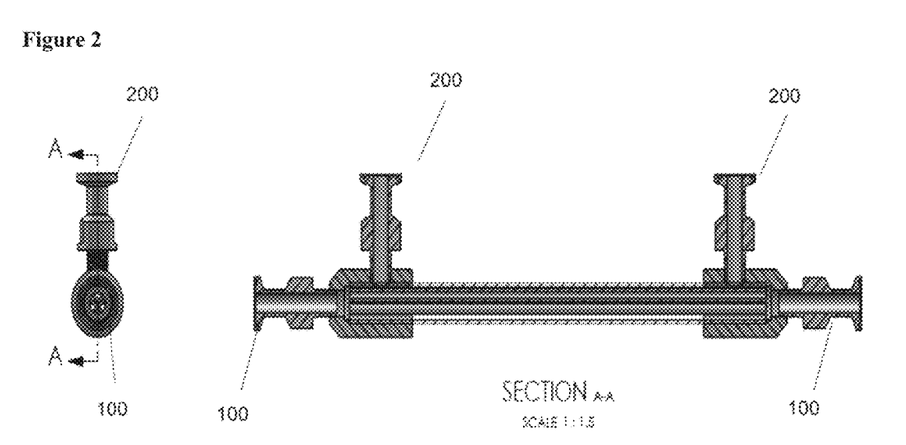
Figure 3:
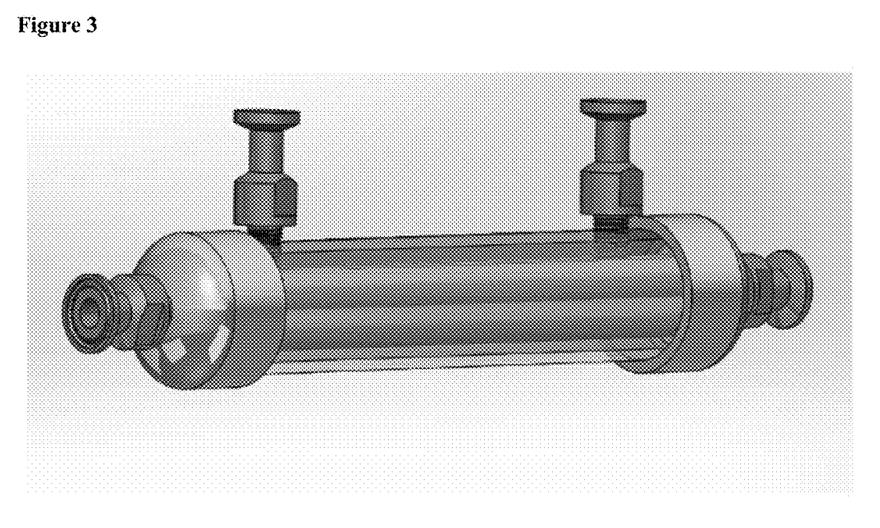
FIG. 3 is a three-dimensional diagram of an exemplary tubular membrane filter element in a Tangential Flow Filtration system according to certain embodiments provided herein.
Figure 4:
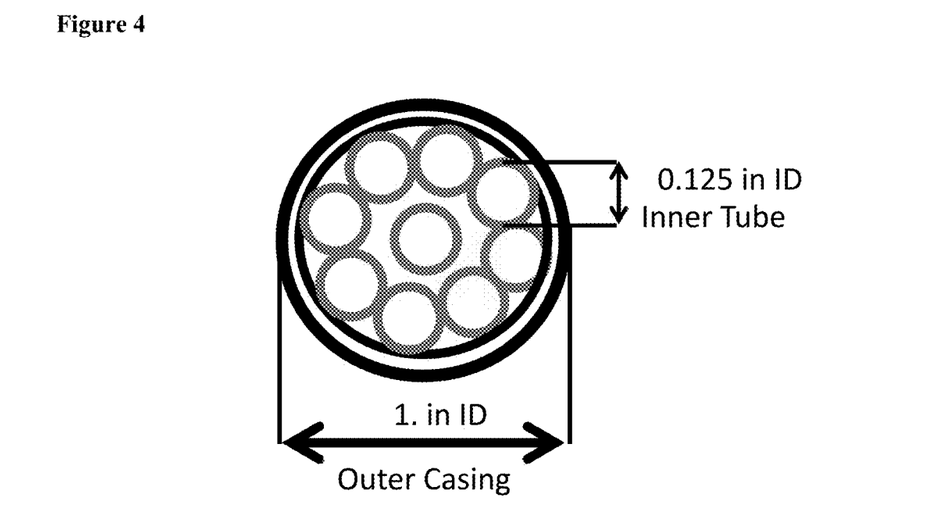
FIG. 4 shows a partial vertical cross section of an exemplary tubular membrane filter comprising 9 porous polyethylene tubes of 0.125 inch internal-diameter (ID) arranged inside a plastic cylindrical casing of 1 inch internal-diameter. Other exemplary configurations in the instant invention may comprise, for example, different numbers, sizes, locations, and/or groupings of the tubes inside the casing.

In some embodiments, macroporous plastic tubular membranes are supported inside a cylindrical casing as shown in FIG. 2. In some embodiments, the tubular membrane filter consists of feed and retentate ports at both ends of the filter which contain cell culture fluid containing mammalian cells and a permeate port for harvesting the viral particles. In certain embodiments, the tubular membrane is made from porous ultra-high-molecular-weight polyethylene (UHM-WPE). In certain embodiments, the tubular membrane filter consists of nine tubular membranes with an internal diameter (ID) of one eighth of an inch (⅛") and a length of 24 inch.

Examples of the plastic material as used herein include, but are not limited to, polyethylene (PE), high density polyethylene (HDPE), Ultra-high-molecular-weight polyethylene (UHMWPE), polypropylene (PP), polytetrafluoroethylene (PTFE), polyvinylidenefluoride (PVDF), ethylvinylacetate (EVA), polycarbonate, nylon 6, thermoplastic urethane (TPU), polyethersulfone (PES), polysulfone (PS), preferably ultra-high-molecular-weight polyethylene (UHMWPE).

In some embodiments, the number and length of the tubular membranes is chosen to provide a sufficient dead volume and maximum surface area for the efficient harvesting of viruses using a tangential flow filtration (TFF)/alternating tangential flow (ATF) system.

Developers are increasingly moving away from small-scale operations and choosing to operate larger-scale apparatus such as stainless steel or single-use bioreactor culture system. It is important to ensure the scalability of the perfusion bioreactor. Other perfusion systems like the WAVE® Bioreactor, which uses a bag as the bioreactor (GE healthcare) allows viral harvest but has an inherent limitation of scalability because of the rocking design which cannot accommodate large bag volumes limiting the cell culture to volumes less than 50 L. The tangential flow filtration (TFF)/alternating tangential flow (ATF) cross filters available in the marketplace are of the hollow-fiber configuration. The limitation of hollow fibers which are made by the spinning process is with respect to the pore size that cannot exceed 0.5 µm-0.65 µm due to an inherent physical limitation of pore creation during the spinning process. This pore size limitation of hollow fiber filters has severely hampered their application in the viral vector and virus-based vaccine manufacturing arena. Viruses tend to aggregate and stick to cell membrane fragments thus creating a virus-virus and/or virus-cell fragment aggregate which cannot permeate through the hollow fiber membrane. This problem not only prohibits the use of hollow fiber membranes for viral particle production larger than the WAVE Bioreactors that use bags as bioreactors, it also prohibits the integration of media exchange with the harvesting step, as indicated above.

There are other considerations such as charge and protein polymer interactions that may limit the penetration of viruses through charged membranes such as polyether sulfone (PES), a typical membrane composition for hollow fiber membranes. The sintered membrane made with UHMWPE plastic material may reduce such charge-charge interactions and allow better permeation of viruses to the permeate side of the tubular membrane compared to the hollow fiber membrane. In addition, the sintered porous membrane which is the subject of this invention can offer much larger pore sizes compared to hollow fibers due to its mode of manufacturing. Hollow fibers are made by extrusion which is known in the art to produce very tight membranes with pore sizes not exceeding 1 micron. Sintered membranes, on the other hand can easily produce pore sizes between 1 µm to 20 µm which allows larger viruses such as lentivirus (80 nm-120 nm) to easily penetrate the membrane. If the membrane is fabricated as a tubule it gives the added advantage of being assembled as a tubular membrane filter with relatively high surface area and a cross-flow geometry to allow sweeping of the membrane in a tangential flow direction and reduced plugging of the membrane compared to a perpendicular flow membrane such as a dead end filter.

In certain embodiments, the tubular cross-flow filters provided herein allow passage of culture media to grow the mammalian cells retained in the bioreactor to a desired cell density prior to infection with the virus of interest and subsequent harvest of the virus particles in the permeate for subsequent purification in the downstream purification train. Thus, the filter elements provided herein can be used for both cell growth and virus purification in a closed, continuous or non-continuous system.

In certain aspects, provided is a process for the culturing of cells by tangential flow filtration (TFF) including alternating tangential flow (ATF) macrofiltration whereas the cell culture comprising cell culture medium and cells, wherein cell culture medium is added to the cell culture, wherein the cell culture is circulated over a filter module comprising tubules wherein the flow within the tubules is a tangential flow and the perfusate from the tubules containing the viral particles is harvested directly without flow interruptions. In this present invention, a viral vector such as a retroviral vector, particularly lentiviral vector, or adeno associated virus (AAV) vector or other viral vaccines or viral particles which are produced in a perfusion bioreactor using alternating tangential flow utilize a cross-flow filter with a plastic membrane of 5 µm-15 µm size to retain the cells while letting viral particles be recovered into the permeate for further downstream purification.

In some embodiments, the tubular filter elements provided herein are suitable for use in a variety of filtration systems and methods. In some embodiments, a tubular filter element is used in a cross flow mode with fluid flowing tangential to the surface of the membrane, in contrast to a dead-end filter where the flow is perpendicular to the surface of the membrane. Cross flow filters can operate in a tangential flow filtration (TFF) mode where the fluid always flows in one direction or in an alternating tangential flow (ATF) where the fluid flow alternates in both directions inside the tubules or hollow fibers. A cross-flow device containing a tubular filter module described herein may include the necessary connections, separation capability, and membrane area to accomplish the tangential flow filtration in the required time.

In some embodiments, the viral harvest is clarified by the cross-flow filter using a tubular membrane having a pore size large enough for the virus to pass through but small enough to retain intact viable cells. In other embodiments, the viral harvest is clarified by the crossflow filter in either a TFF or ATF mode through at least one membrane having a pore size between 5 µm and 15 µm. In still other embodiments, the viral harvest is clarified by cross-flow filter through at least one membrane having a pore size of between 5 µm and 15 µm. In certain embodiments, polyethylene (PE) and/or polyethylene sulfone (PES) membranes are used. In yet other embodiments, the harvesting of the cell culture replicated virus is coupled to the ATF based perfusion. The integration of the cell growth, virus infection and virus recovery steps reduces the number of manipulations, avoids the need for a harvest tank and reduces overall processing time.

Reference hollow fiber filters can serve as a benchmark against which performance of a tubular filter element of the present invention can be measured. Such hollow fiber filters may alternatively be referred to as benchmark hollow fiber filters. Examples of suitable reference hollow fiber filters include, but are not limited to, various ATF filters supplied by Repligen Corporation (Waltham, Mass.), Filtration membranes can be formed, for example, from regenerated cellulose, polyarylsulphones, polyvinylidene fluoride (PVDF), polypropylene, polyester, polyethersulfone (PES), polyethylene, polyethersulfone, polysulfone, polyacrylonitrile, nylon, ethylene chlorotrifluoroethylene, polyimide, polyamide, fluoroethylenepropylene, perfluoroalkoxy, polytetrafluorethylene, polyetheretherketone, polysynidilenesulfide, and polycarbonate.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

EQUIVALENTS

Those skilled in the art will recognize, or be able to ascertain using no more than routine experimentation, many equivalents to the specific embodiments of the present invention described herein. Such equivalents are intended to be encompassed by the following claims.

REFERENCES

Each of the following references are hereby incorporated by reference in its entirety.
Woodside S M, Bowen B D and Piret J M (1998) Mammalian cell retention devices for perfusion bioreactors. Cytotechnology 28: 163-175, 1998
Mercille, et al. (2004) Biotechnology and Bioengineering, 43(9): 833-846.
Kruse, et al., (1965) The Journal of Cell Biology, 27: 273-279.
Jordan, et al, (1992)"Tuning of shear sensitivity of CHO cells and its correlation with the size distribution of cell aggregates" in Animal cell technology: developments, processes and products, eds. Spier, R. E., Griffiths, J. B. and MacDonald, C. London: Butteworth-Heinemann, pp. 418-420.
Snabre, et al., (1987) Biophys. J., 51: 795-807.
Moreira, et al., (1992) "Aggregate suspension cultures of BHK cells" in Animal cell technology: developments, processes and products, eds. Spier, R. E., Griffiths, J. B. and MacDonald, C. London: Butteworth-Heinemann, pp. 411-413.
Maiorella, et al., (1991) Biotechnol. Bioeng., 37(2): 121-126.
A/G Technology Corporation, "Operating Guide" January 1999, N G Technology Corporation.
Yun-Seung Kyung, et al., (1994) Cytotechnology, 14: 183-190.
Anthony S. Lubiniecki, "Large-scale mammalian cell culture technology", CRC Press, 1990, pp. 237-240.
Gary C. Howard, et al., "Basic Methods in Antibody Production and Characterization", CRC Press, 2000, p. 91.
Michael A. Winkler, "Chemical engineering problems in biotechnology", Published by Springer, 1990, pp. 329-330.
Terence Cartwright, "Animal cells as bioreactors", Cambridge University Press, 1994, pp. 72-86.
Shepherd, et al., "Monoclonal antibodies: a practical approach", Oxford University Press, 2000, pp. 137-138.
Maureen Anne Harrison and Ian Fraser Rae, "General techniques of cell culture", Cambridge University Press, 1997, p. 128.
E. C. Beuvery, et al., "Animal Cell Technology: Developments Towards the 21st Century", Springer, 1995, p. 554.
Jerry Shevitz, et al, "Stirred tank perfusion reactors for cell propagation and monoclonal antibody production" in "Advances in Biotechnological Processes" (1989), Alan R. Liss, Inc., Chapter 11, pp. 81-106.
Jones, D. et al., (2003) Biotechnol. Prog. 19: 163-168.
Fallaux et al., (1998). Hum Gene Ther. 9(13): 1909-17.
Furey, J. "Continuous and Scalable Production from a Bioreactor" Poster presentation at the Cell Culture Engineering VII conference, Snowmass Village, Colo., United States of America, Apr. 1-6, 2002.
Furey, J. (2002) Genetic Engineering News, 22(7): 62-63.
Bleckwenn, N. A., Bentley, W. And Shiloach, J. "Production and Glycosylation Analysis of Model proteins from Vaccinia Virus-Mammalian Expression System", poster presentation at the 18th meeting of the European Society for Animal Cell technology (ESACT), Granada, Spain, May 11-14, 2003.
Bleckwenn N. A. et al., "Scalable Protein Production in Anchorage Dependent Mammalian Cells", poster presentation at Bioscience day conference, 2003.
Bleckwenn N. A. et al., entitled "Expression of EGPF Reporter protein with a Recombinant Vaccinia Virus—Comparison of Microcarrier and Cell Sususpension Based Bioreactor Systems" poster presentation at meeting of the American Chemical Society, 2003.
Press release: "Scalable and Reliable Perfusion—Is It Really Possible?" published in the United Kingdom, Apr. 17, 2002.
Jackson, L. R., Trudel. L. J., Fox, J. G. and Lipman, N. S. (1996) "Evaluation of hollow fibre bioreactors as an alternative to murine ascites production for small scale monoclonal antibody production" Journal of Immunological Methods, 189, pp. 217-231.
Piret, J. M. and Cooney, C. L. (1990) "Mammalian cell and protein distributions in ultrafiltration hollow fibre bioreactors" Biotechnology and bioengineering, 36, pp. 902-910.
Falkenberg, F. W., Weichert, H. Krane, M., Bartels, I., Palme, M., Nagels, H.-O. and Feibig, H. (1995) "In vitro production of monoclonal antibodies in high concentration in a new and easy to handle modular minifermenter" Journal of Immunological Methods, 179, pp. 13-29.
Xie, et al., (2002) Biotechnology and Bioengineering, 80(5): 569-579.
Risenberg, et al., (1999) Appl Microbiol Biotechnol, 51:422-430.
Portner, et al., (1995) "Evaluation of Precess Strategies for efficient cultivation of hybridoma cells based on mathematical models," Animal Cell Technology: Developments Towards the 21st Century, Springer, eds. Reuvery, et al., p. 829-831.
Belfort, et al., (1994), "New Development in Membrane Bioreactors," Membrane Processes in Separation and Purification, eds. Crespo and Boddeker, pp. 127-148.
Fuchs, et al., (2002) Jounral of Biotechnology, 93:243-251.
Griffiths (2000), "Immobilized Cultures," Animal Cell Culture: A Practical Approach, Oxford University Press, eds Masters et al., p. 58-67.
Harrison, et al, (1997), General Techniques of cell culture, Cambridge University Press, p. 122-138.
Horwath, (1995) "Facility Design and Validation Considerations for Continuous Cell Culture Processes," Animal Cell Technology: Developments Towards the 21st Century, Springer, eds. Reuvery, et al., p. 553-559.
Maranga, et al., (2006) Biotechnology and Bioengineering, 94(1): 139-150.

Norris, et al. (2002) "Growth of Cell Lines in Bioreactors," Basic Methods in Antibody Production and Characterization, CRC Press, eds. Howard, et al., p. 87-103.

Furey, J., "Continuous cell using the ATF system", (2000) Genetic Engineering News, vol. 20 (10, 15), pp. 52-53.

Voisard, D., et al., Potential of cell retention techniques for large-scale high-density perfusion culture of suspended mammalian cells., Biotechnology and Bioengineering, (2003), vol. 82 (7) pp. 751-765.

Jorjani, P. et al., "Effects of cell density and temperature on oxygen consumption rate for different mammalian cell lines", Biotechnology and Bioengineering (1999), vol. 64 (3) pp. 349-356.

Jones, D. H. et al., "Per. C6 cell for human antibody production crucell's technology maintains human glycosylation patterns", Genetic Engineering News, (2002), vol. 22 (10) pp. 50-54.

Velez, D. et al., "Use of tangential flow filtration in perfusion propagation of hybridoma cells for production of momocional antibodies", Biotechnology and Bioengineering (1989) vol. 33 (7, 20) pp. 938-940.

Woodside S. M. et al., "Mammalian cell retention devices for stirred perfusion bioreactors" Cytotechnology (1998) vol. 28 (1-3) pp. 163-175.

Banik G. G. et al., "Partial and total cell retention in a filtration-based homogeneous perfusion reactor" Biotechnology Prog. (1995) vol. 11, pp. 584-588.

Chisti, Y, Strategies in downstream processing, in: Bioseparation and Bioprocessing: A Handbook (Subramanian, G., editor), Wiley-VCH, New York, pp. 3-30.

John R. W. Masters, Animal Cell Culture: A Practical Approach, Oxford University Press, 2000 ("Masters (2000)"); p. 59.

Joao C. Crespo, Karl W. Boddeker, North Atlantic Treaty Organization. Scientific Affairs Division, "Membrane processes in separation and purification", Springer, 1994 ("Crespo and Boddeker (1994)"); pp. 135-137.

Konstantinov, K. B. et al. "Control of Long-Term Perfusion Chinese Hanster Ovary Cell Culture by Glucose Auxostat" Biotechnol. Prog. vol. 12, pp. 100-109, 1996.

J. Crowley, M. Wubben, J. M. Coco-Martin: "Process Optimization of the Human Cell Line Per.C6 for the Production of Biopharmaceuticals". Presented at Cell Culture Engineering IX, Mar. 7-14, 2004. Cancun, Mexico.

J. Crowley et al. "Pushing mammalian cells to the limit". In DSM Pharma Focus, Issue 14, June 2004. EX-CELL VPRO brochure, printed 2010.

Tharmalinham et al. (2008) "Pluronic enhances the robustness and reduces the cell attachment of mammalian cells", Molecular Biotechnology 39: 167-177.

Shevitz et al. (1989) "Stirred tank perfusion reactors for cell rpopagation and monoclonal antibody production" in "Monoclonal antibodeis: Production and Application" Advances in Biotechnological Processes, vol. 11:81-106.

Gibco Adenovirus Expression Medium (AEM) Information sheet. Invitrogen Corporation, 2003.

van Reis et al., (1991) "Industrial scale harvest of proteins from mammalian cell culture by tangential flow filtration" Biotech. Bioengn. 38, 413-422.

Kawahara et al., (1994) "High-density culture of FM-3A cells using a bioreactor with an external tangential flow filtration device" Cytotechnology 14, 61-66.

Cortin et al., (2004) "High titer adenovirus vector production in 293S cell perfusion culture" Biotechnol. Prog. 20, 858-863.

van Reis et al., (2001) "Membrane separations in biotechnology" Cuurent opinion in Biotechnology 12(2), 208-211.

Notice of Opposition to a European Patent for EP1720972 & Opposition Requests, Fact and Arguments, Opponent Isenbruck Bosl Horschler LLP, Oct. 7, 2014.

Nestola Pl, Peixoto C, Silva R R, Alves P M, Mota J P, Carrondo M J. Improved virus purification processes for vaccines and gene therapy. Biotechnol Bioeng. 2015 May; 112(5):843-57.

What is claimed is:

1. A method of filtering a cell culture media comprising passing a cell culture media comprising mammalian cells and a virus through a plurality of tubular porous membranes of a filter elements enclosed within a casing, wherein each tubular porous membrane filter element comprises a plurality of sintered tubular ultra-high-molecular-weight polyethylene (UHMWPE) porous membranes, wherein at least 95% of the pores in each of the plurality of tubular porous membranes are between 5 μm and −15 μm in size and wherein the internal diameter of each of the plurality of tubular porous membranes is between about 1 mm to about 10 mm, wherein the mammalian cells are retained within the tubular porous membranes and a permeate comprising the virus flows through the pores of the tubular porous membranes into the casing.

2. The method of claim 1, wherein at least 99% of the pores in each of the plurality of tubular porous membranes are between 5 μm and 15 μm in size.

3. The method of claim 1, wherein at least 95% of the pores in each of the plurality of tubular porous membranes are between of 7 μm and 12 μm in size.

4. The method of claim 1, wherein the internal diameter of each of the plurality of tubular porous membranes is between about 1 mm and about 5 mm.

5. The method of claim 1, wherein the virus is a lentivirus, an adeno-associated virus (AAV), and/or an influenza virus.

6. The method of claim 1, wherein the casing has an internal diameter of about 1 to about 30 cm.

7. The method of claim 1, wherein the plurality of tubular porous membranes comprises at least 9 tubular porous membranes.

8. The method of claim 1, wherein the method is a tangential flow filtration perfusion method or an alternating tangential flow perfusion method.

9. The method of claim 1, wherein the virus is a lentivirus.

* * * * *

EX PARTE REEXAMINATION CERTIFICATE (11768th)
United States Patent
Cattaneo et al.

(10) Number: US 10,358,626 C1
(45) Certificate Issued: *Dec. 10, 2020

(54) PERFUSION FILTRATION SYSTEMS (71) Applicant: Artemis Biosystems, Inc., Cambridge, MA (US)

(72) Inventors: Maurizio V. Cattaneo, Boston, MA (US); Remco A. Spanjaard, Brookline, MA (US)

(73) Assignee: ARTEMIS BIOSYSTEMS, INC., Cambridge, MA (US)

Reexamination Request:
No. 90/014,409, Nov. 12, 2019

Reexamination Certificate for:
Patent No.: 10,358,626
Issued: Jul. 23, 2019
Appl. No.: 15/485,866
Filed: Apr. 12, 2017

(*) Notice: This patent is subject to a terminal disclaimer.

Related U.S. Application Data (60) Provisional application No. 62/321,234, filed on Apr. 12, 2016.

(51) Int. Cl.
| | | |
|---|---|---|
| *C12M 1/00* | (2006.01) | |
| *B01D 61/14* | (2006.01) | |
| *B01D 61/18* | (2006.01) | |
| *B01D 63/06* | (2006.01) | |
| *B01D 71/26* | (2006.01) | |
| *C12M 1/12* | (2006.01) | |
| *B01D 61/20* | (2006.01) | |
| *B01D 63/02* | (2006.01) | |
| *C12N 5/00* | (2006.01) | |

(52) U.S. Cl.
CPC ............ *C12M 29/10* (2013.01); *B01D 61/14* (2013.01); *B01D 61/18* (2013.01); *B01D 63/06* (2013.01); *B01D 71/26* (2013.01); *C12M 25/10* (2013.01); *C12M 29/04* (2013.01); *C12M 29/16* (2013.01); *B01D 61/20* (2013.01); *B01D 63/02* (2013.01); *B01D 2315/10* (2013.01); *C07K 2317/10* (2013.01); *C12N 5/00* (2013.01)

(58) Field of Classification Search
CPC ...... C12M 29/10; C12M 29/16; C12M 29/04; C12M 25/10; B01D 71/26; B01D 63/06; B01D 63/02; B01D 2315/10; B01D 61/20; B01D 61/14; C07K 2317/10; C12N 5/00
See application file for complete search history.

(56) References Cited

To view the complete listing of prior art documents cited during the proceeding for Reexamination Control Number 90/014,409, please refer to the USPTO's public Patent Application Information Retrieval (PAIR) system under the Display References tab.

*Primary Examiner* — Elizabeth L McKane (57) ABSTRACT

Provided herein are tubular membrane filter elements, tangential flow filtration systems comprising such filter elements and methods of using such filter elements and filtration systems.

EX PARTE REEXAMINATION CERTIFICATE

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 1 is determined to be patentable as amended.

Claims 2-9, dependent on an amended claim, are determined to be patentable.

1. A method of filtering a cell culture media comprising passing a cell culture media comprising mammalian cells and a virus through a plurality of tubular porous membranes of a filter elements enclosed within a casing,
   wherein each tubular porous membrane filter element comprises a plurality of sintered tubular ultra-high-molecular-weight polyethylene (UHMWPE) porous membranes, wherein at least 95% of the pores in each of the plurality of tubular porous membranes are between 5 μm and [-] 15 μm in size and wherein the internal diameter of each of the plurality of tubular porous membranes is between about 1 mm to about 10 mm,
   wherein the mammalian cells are retained within the tubular porous membranes and a permeate comprising the virus flows through the pores of the tubular porous membranes into the casing.

* * * * *